United States Patent [19]

Fujimura et al.

[11] 4,350,700

[45] Sep. 21, 1982

[54] PHARMACEUTICAL COMPOSITION CONTAINING 1,3,5-SUBSTITUTED BIURET COMPOUND

[75] Inventors: Hajime Fujimura, Kyoto; Yasuzo Hiramatsu, Otsu; Takahiro Yabuuchi, Takarazuka; Masakatu Hisaki, Hikone; Katsuo Takikawa, Naruto; Takaji Honna, Tokushima; Hidekazu Miyake, Tokushima; Makoto Kajitani, Tokushima, all of Japan

[73] Assignee: Taiho Pharmaceutical Company, Limited, Tokyo, Japan

[21] Appl. No.: 257,583

[22] Filed: Apr. 27, 1981

Related U.S. Application Data

[62] Division of Ser. No. 134,411, Mar. 27, 1980.

[30] Foreign Application Priority Data

Mar. 31, 1979 [JP] Japan .................................. 54/38791
Mar. 31, 1979 [JP] Japan .................................. 54/38793

[51] Int. Cl.$^3$ .................................................. A61K 31/44
[52] U.S. Cl. ......................................................... 424/263
[58] Field of Search ........................................... 424/263

[56] References Cited

FOREIGN PATENT DOCUMENTS 819853 9/1959 United Kingdom .
1096006 12/1967 United Kingdom .

OTHER PUBLICATIONS

J.A.C.S. Jun. (1940) 1595-1596.

Primary Examiner—Stanley J. Friedman
Attorney, Agent, or Firm—Murray and Whisenhunt

[57] ABSTRACT

An analgesic, anti-inflammatory or anti-pyretic composition containing 1,3,5-substituted biuret compound of the formula,

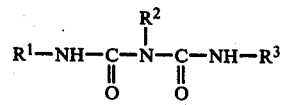

wherein $R^1$ is a hydrogen atom, a lower alkyl group, a substituted lower alkyl group having chlorine atom(s), cyano group(s), dimethylamino group(s), hydroxy group(s), methoxy group(s) or carboxy group(s) as the substituent(s), a lower alkenyl group, a hydroxy group, a methoxy group, an acetyl group or a phenyl group; $R^2$ is a hydrogen atom, a lower alkyl group or a phenyl group; $R^3$ is a phenyl group, a substituted phenyl group having halogen atom(s), trifluoromethyl group(s), methyl group(s), methoxy group(s), methylenedioxy group(s), hydroxy group(s), dimethylamino group(s), carboxy group(s) or carboxymethyl group(s) as the substituent(s), a benzyl group, a pyridyl group, a substituted pyridyl group having methyl group(s) as the substituent(s), a pyridylmethyl group, pyrimidinyl group, a thiazolyl group or a thienyl group, as the active ingredient.

7 Claims, No Drawings

PHARMACEUTICAL COMPOSITION CONTAINING 1,3,5-SUBSTITUTED BIURET COMPOUND

This is a Divisional application of Ser. No. 134,411, filed Mar. 27, 1980.

The present invention relates to a pharmaceutical composition containing a 1,3,5-substituted biuret compound. More particularly, the present invention relates to an analgesic, anti-inflammatory or anti-pyretic composition containing as the active ingredient 1,3,5-substituted biuret compound of the formula (1),

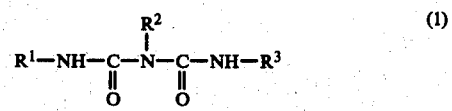

wherein $R^1$ is a hydrogen atom, a lower alkyl group, a substituted lower alkyl group having chlorine atom(s), cyano group(s), dimethylamino group(s), hydroxy group(s), methoxy group(s) or carboxy group(s) as the substituent(s), a lower alkenyl group, a hydroxy group, a methoxy group, an acetyl group or a phenyl group; $R^2$ is a hydrogen atom, a lower alkyl group or a phenyl group; $R^3$ is a phenyl group, a substituted phenyl group having halogen atom(s), trifluoromethyl group(s), methyl group(s), methoxy group(s), methlenedioxy group(s), hydroxy group(s), dimethylamino group(s), carboxyl group(s) or carboxymethyl group(s) as the substituent(s), a benzyl group, a pyridyl group, a substituted pyridyl group having methyl group(s) as the substituent(s), a pyridylmethyl group, a pyrimidinyl group, a thiazolyl group or a thienyl group.

Hitherto, some of 1,3,5-substituted biuret compounds represented by the formula (1) are known. On the other hand, although the definitions of the substituents in the formula (1) are different, other substituted biuret compounds having the basic structure of the formula,

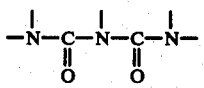

which is common to the formula (1) are known.

There have been reported that some of such known substituted biuret compounds, especially the latter compounds having the above-mentioned basic structure, have hypotensive, sedative or anti-convulsive activity. However, the prior art has not been aware that either 1,3,5-substituted biuret compounds represented by the general formula (1) or other known biuret compounds, having the above-mentioned basic structure which is common to the general formula (1), have analgesic, anti-inflammatory or anti-pyretic activity. [cf. British pat. No. 1,096,006; British Pat. No. 819,853 and J. Amer. Chem. Soc., 62, 1595 (1940)]

The present invention is based on the facts that the 1,3,5-substituted biuret compounds represented by the general formula have analgesic, anti-inflammatory or anti-pyretic activity.

The object of the present invention is to provide novel 1,3,5-substituted biuret compounds.

Another object of the present invention is to provide an analgesic, anti-inflammatory or anti-pyretic composition containing 1,3,5-substituted biuret compound as the active ingredient.

Among the 1,3,5-substituted biuret compounds of the formula (1), the following compounds are novel ones.
1,3-Dimethyl-5-(2-chlorophenyl)biuret
1,3-Dimethyl-5-(2-trifluoromethylphenyl)biuret
1,3-Dimethyl-5-(3,4-methylenedioxyphenyl)biuret
1,3-Dimethyl-5-(2-carboxyphenyl)biuret
1,3-Dimethyl-5-(4-carboxymethylphenyl)biuret
1,3-Dimethyl-5-(2-pyridylmethyl)biuret
1,3-Dimethyl-5-(4-methyl-2-pyridyl)biuret
1,3-Dimethyl-5-(2-pyrimidinyl)biuret
1-Methyl-3-ethyl-5-phenylbiuret
1-Ethyl-5-phenylbiuret
1-Ethyl-5-(2-chlorophenyl)biuret
1-Ethyl-5-(3-chlorophenyl)biuret
1-Ethyl-5-(3,4-dichlorophenyl)biuret
1-Ethyl-5-(4-methoxyphenyl)biuret
1-Ethyl-5-benzylbiuret
1-Ethyl-5-(2-pyridyl)biuret
1-Ethyl-3-methyl-5-phenylbiuret
1-Ethyl-3-methyl-5-(4-fluorophenyl)biuret
1-Ethyl-3-methyl-5-(4-dimethylaminophenyl)biuret
1-Ethyl-3-methyl-5-(4-hydroxyphenyl)biuret
1-Ethyl-3-methyl-5-(4-methoxyphenyl)biuret
1-Ethyl-3-methyl-5-(3,4-dimethoxyphenyl)biuret
1-Ethyl-3-methyl-5-(3,4,5-trimethoxyphenyl)biuret
1-Ethyl-3-methyl-5-(4-methylphenyl)biuret
1-Ethyl-3-methyl-5-(3,4-dimethylphenyl)biuret
1-Ethyl-3-methyl-5-(2-thenyl)biuret
1-n-Propyl-3-methyl-5-phenylbiuret
1-Isopropyl-3-methyl-5-phenylbiuret
1-Propenyl-5-phenylbiuret
1-Propenyl-3-methyl-5-phenylbiuret
1-n-Propyl-5-phenylbiuret
1-n-Propyl-3-methyl-5-phenylbiuret
1-n-Propyl-5-benzylbiuret
1-Isobutyl-3-methyl-5-phenylbiuret
1-(1-Methylpropyl)-3-methyl-5-phenylbiuret
1-tert-Butyl-3-methyl-5-phenylbiuret
1-n-Pentyl-3-methyl-5-phenylbiuret
1-(2-Chloroethyl)-3-methyl-5-phenylbiuret
1-(2-Cyanoethyl)-3-methyl-5-phenylbiuret
1-(2-Dimethylaminoethyl)-3-methyl-5-phenylbiuret
1-(2-Hydroxyethyl)-3-methyl-5-phenylbiuret
1-(2-Methyl-2-hydroxypropyl)-3-methyl-5-phenylbiuret
1-(2,3-Dihydroxypropyl)-3-methyl-5-phenylbiuret
1-(2-Methoxyethyl)-3-methyl-5-phenylbiuret
1-Carboxymethyl-3-methyl-5-phenylbiuret
1-Acetyl-3-methyl-5-phenylbiuret
1-Hydroxy-3-methyl-5-phenylbiuret
1-Methoxy-3-methyl-5-phenylbiuret The 1,3,5-substituted biuret compound of the formula (1) can be prepared by any processes shown below.

REACTION PROCESS—A

Reaction of an urea compound of the formula (2) or (4) with an isocyanate of the formula (3) or (5) to obtain the 1,3,5-substituted biuret compound of the formula (1) is shown as follows:

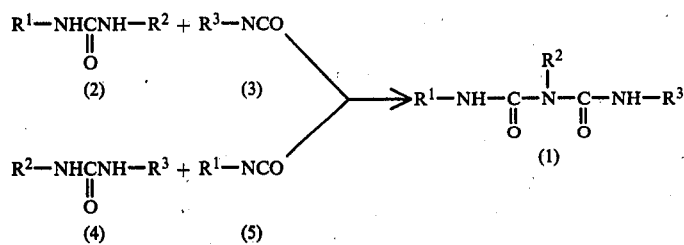

In this reaction process A, the reaction of the urea with the isocyanate may be carried out in the presence or absence of a solvent. The solvent used in this reaction is not subjected to any specific restriction and any known inert type which gives no adverse effect to the reaction can be used. Among the examples of the solvents are ethers such as ether, dioxane, tetrahydrofuran and the like; halogenated lower alkanes such as methylene chloride, chloroform, carbon tetrachloride and the like; aromatic hydrocarbons such as benzene, toluene, xylene and the like. The ratio of amount of the urea and the isocyanate in this reaction is not subjected to any specific restriction and may be suitably selected from a wide range, and usually, it is desirable that they are used in equimolar quantity respectively. The reaction temperature is also not subjected to any particular restriction and may be suitably selected from a wide range, and usually the reaction can advantageously be carried out at a room temperature to the boiling point of the solvent used generally within the range of 20° to 200° C. The obtained 1,3,5-substituted biuret compound of the formula (1) can be isolated by usual separation means.

REACTION PROCESS—B

Reaction of an allophanoyl chloride of the formula (6) or (8) with an amine of the formula (7) or (9) to obtain 1,3,5-substituted biuret compound of the formula (1) is shown as follows:

type which gives no adverse effect to the reaction can be used. Among the examples of the solvents are halogenated lower alkanes such as methylene chloride, chloroform, carbon tetrachloride and the like; aromatic hydrocarbons such as benzene, toluene, xylene and the like. If necessary, basic compounds such as trialkylamine, pyridine and the like may be used as suitable condensation agent. The ratio of amount of the allophanoyl chloride and the amine in this reaction is not subjected to any specific restriction and may be suitably selected from a wide range, and usually it is desirable that the amine (7) or (9) is used in equimolar to 2 times the molar quantity of the allophanoyl chloride (6) or (8). The reaction temperature is also not subjected to any particular restriction, and the reaction can advantageously be carried out at −20° to +50° C. Thus formed 1,3,5-substituted biuret compound of the formula (1) can be isolated by usual separation means.

The allophanoyl chloride of the formula (6) or (8) used as the starting material in the reaction process—B is usually known compound and if necessary, it can be prepared by reacting the urea compound of the formula (2) or (4) used in the reaction process—A with phosgene according to known method [e.g. J. Org. Chem., vol. 29, pp. 2401 (1964)].

REACTION PROCESS—C

Reaction of a 1,3-diazetidine-2,4-dione of the formula

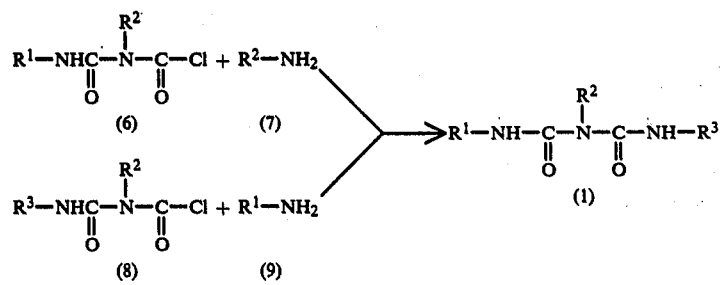

In this reaction process B, the reaction of the allophanoyl chloride with the amine may be carried out in a solvent. The solvent used in this reaction is not subjected to any specific restriction and any known inert

(10) or (11) with an amine of the formula (7) or (9) to obtain 1,3,5-substituted biuret compound of the formula (1) is shown as follows:

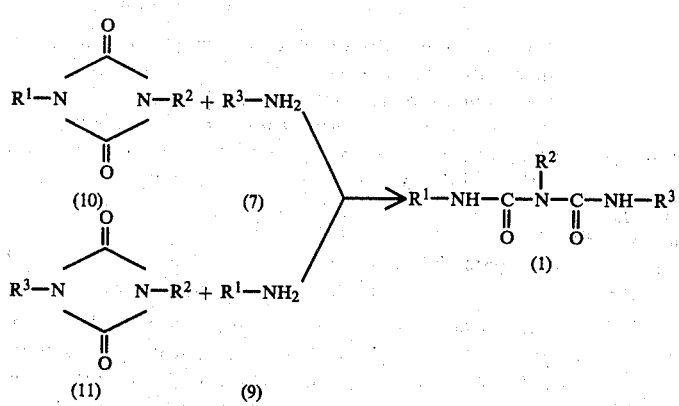

In this reaction process—C, the reaction of the 1,3-diazetidine-2,4-dione with the amine may usually be carried out in a solvent. The solvent used in this reaction is not subjected to any specific restriction and any known inert type which gives no adverse effect to the reaction can be used. Generally, water, acetone, acetonitrile and the like may be used as the solvent. The ratio of amount of the 1,3-diazetidine-2,4-dione and the amine in this reaction is not subjected to any specific restriction and may be suitably selected from a wide range, and usually, it is desirable that the amine (7) or (9) is used in equimolar to 2 times the molar quantity of the 1,3-diazetidine-2,4-dione (10) or (11). The reaction temperature is also not subjected to any particular restriction, and the reaction can advantageously be carried out at a room temperature to about 100° C. The thus formed 1,3,5-substituted biuret compound of the formula (1) can be isolated by usual separation means. The 1,3-diazetidine-2,4-dione of the formula (10) or (11) used as the starting material in the reaction process—C is usually known compound and if necessary, it can be prepared by reacting the allophanoyl chloride compound of the formula (6) or (8) in the reaction process—B with boron trichloride according to known method [e.g. Angew. Chem. International Edition, vol. 9, pp. 373 (1970)].

Reaction Process—D

When preparing 1,3,5-substituted biuret compound of the formula (1), wherein $R^1=R^2$ or $R^2=R^3$, it is prepared by reacting a 1,3,5-oxadiazine-2,4,6-trione of the formula (12) or (13) with an amine of the formula (7) or (9) as follows:

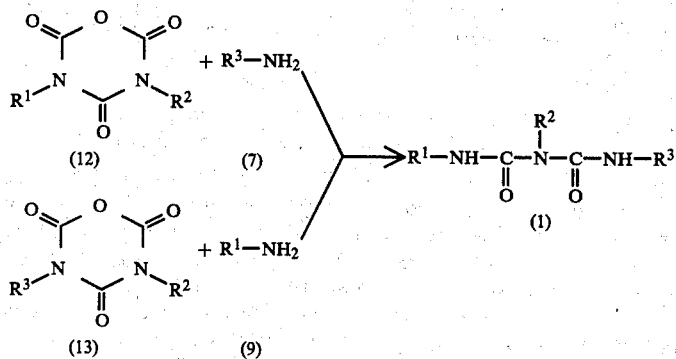

In this reaction process—D, the reaction of the 1,3,5-oxadiazine-2,4,6-trione with the amine may usually be carried out in a solvent. The solvent used in this reaction is not subjected to any specific restriction and any known inert type which gives no adverse effect to the reaction can be used. Generally, acetonitrile, tetrahydrofuran and the like may be used as the solvent. The ratio of amount of the 1,3,5-oxadiazine-2,4,6-trione and the amine in this reaction is not subjected to any specific restriction and may be suitably selected from a wide range, and usually, it is desirable that the amine (7) or (9) is used in equimolar to 2 times the molar quantity of the 1,3,5-oxadiazine-2,4,6-trione (12) or (13). The reaction temperature is also not subjected to any particular restriction, and the reaction can advantageously be carried out at a room temperature to about 100° C. The thus formed 1,3,5-oxadiazine-2,4,6-trione of the formula (1) can be isolated by usual separation means.

The 1,3,5-oxadiazine-2,4,6-trione of the formula (12) or (13) used as the starting material in this reaction process—D is usually known compound and if necessary, it can easily be prepared by reacting the isocyanate of the formula (3) or (5) used in the reaction process—A with carbon dioxide according to known method [e.g. Bull. Soc. Chim. Fr., 1974, 1497].

Most of the 1,3,5-substituted biuret compounds of the formula (1) of the present invention [that is, all compounds, except those of formula (1') below] are useful as analgesic agents, anti-inflammatory agents or antipyretic agents. However, among of those compounds, 1,3,5-substituted biuret compounds of the formula (1')

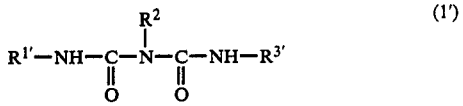

(1')

wherein $R^{1'}$ is a lower alkyl group, a substituted lower alkyl group having chlorine atoms(s), cyano group(s), dimethylamino group(s) or hydroxyl group(s) as the substituent(s); a lower alkenyl group or a methoxy group; $R^2$ is a hydrogen atom, a lower alkyl group, or a phenyl group; $R^{3'}$ is a phenyl group, a substituted phenyl group having halogen atom(s), trifluoromethyl group(s), methoxy group(s), methylenedioxy group(s), dimethylamino group(s) or hydroxy group(s) as the substituent(s), a benzyl group, a pyridyl group, a substituted pyridyl group having methyl group(s) as the substituent(s), a thiazolyl group or a thienyl group, are useful only as anti-inflammatory agents.

The 1,3,5-substituted biuret compound of the formula (1) of the present invention can be administered in the range of from 10 to 2,000 mg per day, preferably from 50 to 1,000 mg per day, for an adult, as a analgesic, anti-inflamatory or anti-pyretic agent. The administration of the compound is carried out by dividing the above-mentioned daily dosage into 2 or 3 portions. Said dosage of the compound may be adjusted in consideration of the clinical conditions and age of the patient.

The administration may be carried out in the form of peroral preparations, injection preparations, suppository preparations for rectal use, topical preparations and the like.

An analgesic, anti-inflammatory or anti-pyretic composition containing the present 1,3,5-substituted biuret compound of the formula (1) is prepared and administered by formulating with conventional pharmaceutically acceptable carriers or excipients through a common method.

Peroral preparations such as tablets, capsules, granules, powders, etc. may contain excipients used generally in the art. Said excipients are exemplified such as calcium carbonate, calcium phasphates, starch, sucrose, lactose, talc, magnesium stearate, gelatine, polyvinylpyrrolidone, gum arabic, sarbitol, microcrystalline cellulose, polyethyleneglycol, carboxymethylcellulose, silica polyvinylacetal diethylamino acetate, hydroxypropyl methylcellulose, shellac, etc. Further, the tablets may be coated with a suitable coating by a common method known in the arts. Peroral liquid form preparations may be of aqueous or oily suspensions, syrups, elixiers and the like and are prepared by common methods. Injection preparations may be of aqueous or oily suspensions, powdery or lyophilyzed preparations which is dissolved upon use. These preparations may be prepared by a common method.

The present substituted biuret compound may be administered as a suppository composition for rectal use, which may be contain pharmaceutically acceptable carriers, known in the art, such as polyethylene glycols, lanoline, cacao butter, fatty acid triglycerides, and the like.

As to preparations for topical use, the substituted biuret compound of the formula (1) of the present invention may be administered in the form of an ointment or cream which is prepared by formulating with a suitable ointment base and other additives by common method.

EXAMPLES OF THE INVENTION

The present invention is further explained in detail by illustrating examples of synthesis of the substituted biuret compounds in Table 1; and pharmacological tests including analgesic activity test, anti-inflammatory activity test and anti-pyretic activity test in Table 2 together with examples of pharmaceutical preparations.

EXAMPLE 1

Synthesis of 1-ethyl-5-phenylbiuret (Compound No. 23 in Table 1) by reaction process—A In 50 ml of anhydrous dioxane, 3.5 g (0.04 mol) of ethyl urea was dissolved, and under stirring 4.8 g (0.04 mol) of phenylisocyanate was added thereinto. The reaction was carried out at a room temperature for 15 hours, then the solvent was removed by distillation under a reduced pressure. The residue thus obtained was recrystallized from ethanol-water to obtain 4.6 g (yield 55%) of 1-ethyl-5-phenylbiuret having a melting point of 80°–81.5° C.

EXAMPLE 2

Synthesis of 1,3-dimethyl-5-phenylbiuret (Compound No. 3 in Table 1) by reaction process—A In 50 ml of anhydrous dioxane, 3.5 g (0.04 mol) of 1,3-dimethyl urea was dissolved, and under stirring 4.8 g (0.04 mol) of phenylisocyanate was added thereinto. The reaction was carried out at a room temperature for 15 hours, then the reaction mixture was treated a procedure same as in Example 1. The residue thus obtained was recrystallized from ethanol-petroleum ether to obtain 5.0 g (yield 60%) of 1,3-dimethyl-5-phenylbiuret having a melting point of 93°–95° C.

EXAMPLE 3

Synthesis of 1-ethyl-3-methyl-5-phenylbiuret (Compound No. 31 in Table 1) by reaction process—B In 50 ml of anhydrous tetrahydrofuran, 9.0 g (0.2 mol) of ethylamine was dissolved, and under cooling below 0° C. with stirring, a solution prepared by dissolving 21.3 g (0.1 mol) of 2-methyl-4-phenylallophanoyl chloride into 50 ml of anhydrous tetrahydrofuran was added by drop-wise. The reaction was continued at a room temperature for 1 hour, the solvent was then removed by distillation under a reduced pressure. To the residue thus obtained was added water and the precipitate thus formed was separated by filtration and dried, and recrystallized from ether-petroleum ether to obtain 17.7 g (yield 80%) of 1-ethyl-3-methyl-5-phenylbiuret having a melting point of 80.5°–81.5° C.

EXAMPLE 4

Synthesis of 1-phenyl-3,5-diphenylbiuret (Compound No. 22 in Table 1) by reaction process—C In 30 ml of acetonitrile, 6.0 g (0.025 mol) of 1,3-diphenyl-1,3-diazetidine-2,4-dione was added. Then 3.9 ml (0.05 mol) of aqueous solution (40%) of methylamine was added dropwise thereinto with stirring. The reaction was continued at 50° C. for 0.5 hours, then the solvent was removed by distillation under a reduced pressure. The residue thus obtained was recrystallized from ethanol to obtain 5.1 l g (yield 76%) of 1-methyl-3,5-diphenylbiuret having a melting point of 145°–147° C.

EXAMPLE 5

Synthesis of 1,3-dimethyl-5-(2-pyridyl)biuret (Compound No. 14 in Table 1) by reaction process—D In 50 ml of acetonitrile, 5.0 g (0.0316 mol) of 3,5-dimethyl-2,4,6-trioxohydro-1,3,5-oxadiazine and 3.0 g (0.0319 mol) of 2-aminopyridine were added. The reaction was continued under refluxing condition for 7 hours. After the reaction was completed, water was added to the reaction mixture and was filtered. The filtrate thus obtained was extracted with chloroform, and the extracted liquid was dried with anhydrous sodium sulfate and the chloroform was removed by distillation. The residue thus obtained was recrystallized from benzene to obtain 3.0 g (yield 46%) of 1,3-dimethyl-5-(2-pyridyl)biuret having a melting point of 112°–115° C.

In the following Table 1, there are mentioned the physico-chemical properties of 1,3,5-substituted biuret compounds of the formula (1) including the compounds prepared in Examples 1–5.

TABLE 1

$R^1-NH-\underset{\underset{O}{\|}}{C}-\underset{R^2}{N}-\underset{\underset{O}{\|}}{C}-NH-R^3$

| Compound No. | $R^1$ | $R^2$ | $R^3$ | Reaction process | Mp, (°C.) | UV$\lambda_{max}^{Cyclohexane}$ m$\mu$ ($\epsilon$) | Molecular formula | Elemental analysis (%) Calculated (Found) C | H | N |
|---|---|---|---|---|---|---|---|---|---|---|
| 1* | H | —CH$_3$ | phenyl | B | 188–190 | 243.5 (17700) | C$_9$H$_{11}$N$_3$O$_2$ | 55.95 (55.62) | 5.74 (5.57) | 21.75 (21.61) |
| 2* | —CH$_3$ | —H | phenyl | A | 121–122 | 240 (19600) | C$_9$H$_{11}$N$_3$O$_2$ | 55.95 (55.91) | 5.74 (5.59) | 21.75 (21.77) |
| 3* | —CH$_3$ | —CH$_3$ | phenyl | A | 93–95 | 244 (17900) | C$_{10}$H$_{13}$N$_3$O$_2$ | 57.96 (58.09) | 6.32 (6.39) | 20.28 (20.18) |
| 4* | —CH$_3$ | —CH$_3$ | 2-F-phenyl | B | 148–150 | 240.5 (25800) | C$_{10}$H$_{12}$FN$_3$O$_2$ | 53.33 (53.22) | 5.37 (5.30) | 18.66 (18.32) |
| 5 | —CH$_3$ | —CH$_3$ | 2-Cl-phenyl | A | 168.5–170.5 | 247.5 (20700) | C$_{10}$H$_{12}$ClN$_3$O$_2$ | 49.70 (49.99) | 5.00 (4.96) | 17.39 (17.32) |
| 6* | —CH$_3$ | —CH$_3$ | 4-Cl-phenyl | A | 143–145 | 250.5 (25000) | C$_{10}$H$_{12}$ClN$_3$O$_2$ | 49.70 (49.70) | 5.00 (5.09) | 17.39 (17.18) |
| 7 | —CH$_3$ | —CH$_3$ | 2-CF$_3$-phenyl | B | 115–117 | 243 (17200) | C$_{11}$H$_{12}$F$_3$N$_3$O$_2$ | 48.00 (48.30) | 4.39 (4.43) | 15.27 (15.38) |
| 8* | —CH$_3$ | —CH$_3$ | 4-OCH$_3$-phenyl | B | 110–111 | 249 (20300) | C$_{11}$H$_{15}$N$_3$O$_3$ | 55.69 (55.66) | 6.37 (6.63) | 17.71 (17.50) |
| 9 | —CH$_3$ | —CH$_3$ | 3,4-methylenedioxy-phenyl | B | 176–178 | 256 (13500) | C$_{11}$H$_{13}$N$_3$O$_4$ | 52.59 (52.61) | 5.22 (5.19) | 16.72 (16.43) |
| 10 | —CH$_3$ | —CH$_3$ | 2-HOOC-phenyl | B | 178–179 | 250 (16400) | C$_{11}$H$_{13}$N$_3$O$_4$ | 52.59 (52.58) | 5.22 (5.12) | 16.72 (16.70) |
| 11 | —CH$_3$ | —CH$_3$ | 4-(CH$_2$COOH)-phenyl | D | 195–196 | 248.5 (21600) | C$_{12}$H$_{15}$N$_3$O$_4$ | 54.33 (54.29) | 5.70 (5.95) | 15.84 (15.79) |
| 12* | —CH$_3$ | —CH$_3$ | —CH$_2$-phenyl | B | 118–119 | | C$_{11}$H$_{15}$N$_3$O$_2$ | 59.71 (59.70) | 6.83 (7.01) | 18.99 (18.97) |
| 13 | —CH$_3$ | —CH$_3$ | —CH$_2$-(2-pyridyl) | D | 101.5–102.5 | 262 (2700) | C$_{10}$H$_{14}$N$_4$O$_2$ | 54.04 (54.14) | 6.35 (6.26) | 25.21 (25.41) |

TABLE 1-continued

| Compound No. | R¹ | R² | R³ | Reaction process | Mp, (°C.) | UV$\lambda_{max}^{Cyclohexane}$ mμ (ε) | Molecular formula | Elemental analysis (%) Calculated (Found) C | H | N |
|---|---|---|---|---|---|---|---|---|---|---|
| 14* | —CH₃ | —CH₃ | 3-pyridyl | D | 112–115 | 238 (19400) | C₉H₁₂N₄O₂ | 51.92 (51.88) | 5.81 (5.93) | 26.91 (27.04) |
| 15* | —CH₃ | —CH₃ | 4-pyridyl | D | 149–150 | 242 (15400) | C₉H₁₂N₄O₂ | 51.92 (52.01) | 5.81 (5.74) | 26.91 (26.95) |
| 16* | —CH₃ | —CH₃ | 2-pyridyl | D | 177–178 | | C₉H₁₂N₄O₂ | 51.92 (51.80) | 5.81 (5.88) | 26.91 (27.00) |
| 17* | —CH₃ | —CH₃ | 4-methyl-2-pyridyl | D | 146–147 | 239 (19200) | C₁₀H₁₄N₄O₂ | 54.04 (53.86) | 6.35 (6.38) | 25.21 (25.20) |
| 18 | —CH₃ | —CH₃ | 4-methyl-pyridyl | D | 120–121.5 | 240 (20300) | C₁₀H₁₄N₄O₂ | 54.04 (53.73) | 6.35 (6.42) | 25.21 (25.16) |
| 19 | —CH₃ | —CH₃ | pyrazinyl | D | 229–231 (decomposed) | 272 (3100) | C₈H₁₁N₅O₂·HCl | 39.13 (38.92) | 4.93 (5.03) | 28.52 (28.67) |
| 20* | —CH₃ | —CH₃ | thiazolyl | D | 166–167 | 263 (11500) | C₇H₁₀N₄O₂S | 39.24 (39.26) | 4.70 (4.81) | 26.15 (26.03) |
| 21 | —CH₃ | —C₂H₅ | phenyl | B | 84–86 | 244 (19700) | C₁₁H₁₅N₃O₂ | 59.71 (60.06) | 6.83 (7.05) | 18.99 (19.13) |
| 22* | —CH₃ | phenyl | phenyl | C | 145–147 | | C₁₅H₁₅N₃O₂ | 66.90 (66.70) | 5.61 (5.54) | 15.60 (15.53) |
| 23 | —C₂H₅ | —H | phenyl | A | 80–81.5 | 242 (21700) | C₁₀H₁₃N₃O₂ | 57.96 (58.05) | 6.32 (6.48) | 20.28 (20.25) |
| 24 | —C₂H₅ | —H | 2-chlorophenyl | A | 152–154 | 245.5 (20300) | C₁₀H₁₂ClN₃O₂ | 49.70 (49.95) | 5.00 (4.86) | 17.39 (17.08) |
| 25 | —C₂H₅ | —H | 3-chlorophenyl | A | 120–122 | 244.5 (22300) | C₁₀H₁₂ClN₃O₂ | 49.70 (49.98) | 5.00 (4.82) | 17.39 (17.25) |
| 26* | —C₂H₅ | —H | 4-chlorophenyl | A | 175–177 | 248 (25900) | C₁₀H₁₂ClN₃O₂ | 49.70 (49.97) | 5.00 (5.13) | 17.39 (17.24) |
| 27 | —C₂H₅ | —H | 3,4-dichlorophenyl | A | 184.5–185.5 | 250.5 (26600) | C₁₀H₁₁Cl₂N₃O₂ | 43.50 (43.30) | 4.02 (4.01) | 15.22 (15.22) |

TABLE 1-continued $R^1-NH-\underset{\underset{O}{\|}}{C}-\underset{\underset{R^2}{|}}{N}-\underset{\underset{O}{\|}}{C}-NH-R^3$

| Compound No. | R[1] | R[2] | R[3] | Reaction process | Mp, (°C.) | UV$\lambda_{max}^{Cyclohexane}$ mμ (ε) | Molecular formula | Elemental analysis (%) Calculated (Found) | | |
|---|---|---|---|---|---|---|---|---|---|---|
| | | | | | | | | C | H | N |
| 28 | —C$_2$H$_5$ | —H | —⌬—OCH$_3$ | A | 141–142 | 248 (21400) | C$_{11}$H$_{17}$N$_3$O$_4$ | 55.69 (55.60) | 6.37 (6.13) | 17.71 (17.41) |
| 29 | —C$_2$H$_5$ | —H | —CH$_2$—⌬ | A | 108–110 | | C$_{11}$H$_{15}$N$_3$O$_2$ | 59.71 (59.85) | 6.83 (6.89) | 18.88 (19.14) |
| 30 | —C$_2$H$_5$ | —H | pyridyl | A | 125–126 | 240 (19800) | C$_9$H$_{12}$N$_4$O$_2$ | 51.92 (51.83) | 5.81 (5.94) | 26.91 (26.80) |
| 31 | —C$_2$H$_5$ | —CH$_3$ | —⌬ | B | 80.5–81.5 | 244 (19900) | C$_{11}$H$_{15}$N$_3$O$_2$ | 59.71 (59.78) | 6.83 (7.03) | 18.99 (18.69) |
| 32 | —C$_2$H$_5$ | —CH$_3$ | —⌬—F | B | 112–114 | 241 (20000) | C$_{11}$H$_{14}$FN$_3$O$_2$ | 55.22 (55.08) | 5.90 (6.04) | 17.56 (17.24) |
| 33 | —C$_2$H$_5$ | —CH$_3$ | —⌬—N(CH$_3$)$_2$ | B | 116–118 | 263 (22300) | C$_{13}$H$_{20}$N$_4$O$_2$ | 59.07 (58.93) | 7.63 (7.61) | 21.20 (21.20) |
| 34 | —C$_2$H$_5$ | —CH$_3$ | —⌬—OH | B | 151–153 | 248 (15100) | C$_{11}$H$_{15}$N$_3$O$_3$ | 55.69 (55.60) | 6.37 (6.29) | 17.71 (17.80) |
| 35 | —C$_2$H$_5$ | —CH$_3$ | —⌬—OCH$_3$ | B | 58–59 | 249 (22000) | C$_{12}$H$_{17}$N$_3$O$_3$ | 57.36 (57.13) | 6.82 (6.96) | 16.72 (16.41) |
| 36 | —C$_2$H$_5$ | —CH$_3$ | —⌬(OCH$_3$)$_2$ | B | 98–100 | 252 (14700) | C$_{13}$H$_{19}$N$_3$O$_4$ | 55.51 (55.63) | 6.81 (6.87) | 14.94 (14.54) |
| 37 | —C$_2$H$_5$ | —CH$_3$ | —⌬(OCH$_3$)$_3$ | B | 104–106 | 256 (15400) | C$_{14}$H$_{19}$N$_3$O$_5$ | 54.01 (53.94) | 6.80 (6.79) | 13.50 (13.74) |
| 38 | —C$_2$H$_5$ | —CH$_3$ | —⌬—CH$_3$ | B | 88–90 | 246 (20100) | C$_{12}$H$_{17}$N$_3$O$_2$ | 61.26 (61.23) | 7.28 (7.46) | 17.86 (17.61) |
| 39 | —C$_2$H$_5$ | —CH$_3$ | —⌬(CH$_3$)$_2$ | B | 66–68 | 247 (18800) | C$_{13}$H$_{19}$N$_3$O$_2$·½H$_2$O | 60.45 (60.07) | 7.80 (7.71) | 16.27 (16.09) |
| 40 | —C$_2$H$_5$ | —CH$_3$ | thienyl | B | 112–114 | 271 (11400) 267 (11600) | C$_9$H$_{13}$N$_3$O$_2$S | 47.56 (47.78) | 5.77 (5.77) | 18.49 (18.38) |
| 41 | —(CH$_2$)$_2$CH$_3$ | —CH$_3$ | —⌬ | B | 74–76 | 244 (20800) | C$_{12}$H$_{17}$N$_3$O$_2$ | 61.26 (61.22) | 7.28 (7.52) | 17.86 (17.47) |
| 42* | —(CH$_2$)$_2$CH$_3$ | —H | —CH$_2$—⌬ | A | 85.5–88 | not available | C$_{12}$H$_{17}$N$_3$O$_2$ | 61.26 (61.33) | 7.28 (7.20) | 17.86 (17.68) |
| 43 | —CH(CH$_3$)$_2$ | —CH$_3$ | —⌬ | B | 92–93.5 | 243 (20500) | C$_{12}$H$_{17}$N$_3$O$_2$ | 61.26 (61.67) | 7.28 (7.49) | 17.86 (17.83) |
| 44 | —CH$_2$CH=CH$_2$ | —H | —⌬ | A | 75–78 | 253 (20500) | C$_{11}$H$_{13}$N$_3$O$_2$ | 60.26 (59.95) | 5.98 (6.06) | 19.17 (19.10) |

TABLE 1-continued $$R^1-NH-\underset{\underset{O}{\|}}{C}-\underset{R^2}{N}-\underset{\underset{O}{\|}}{C}-NH-R^3$$

| Compound No. | $R^1$ | $R^2$ | $R^3$ | Reaction process | Mp, (°C.) | UV$\lambda_{max}^{Cyclohexane}$ m$\mu$ ($\epsilon$) | Molecular formula | Elemental analysis (%) Calculated (Found) C | H | N |
|---|---|---|---|---|---|---|---|---|---|---|
| 45 | $-CH_2CH=CH_2$ | $-CH_3$ | $-\langle O \rangle$ | B | 79–80 | 243 (19900) | $C_{12}H_{15}N_3O_2$ | 61.79 (61.75) | 6.48 (6.71) | 18.01 (18.15) |
| 46 | $-(CH_2)_3CH_3$ | $-H$ | $-\langle O \rangle$ | A | 106.5–108.5 | 241.5 (22400) | $C_{12}H_{17}N_3O_2$ | 61.26 (61.03) | 7.28 (7.19) | 17.86 (17.92) |
| 47 | $-(CH_2)_3CH_3$ | $-CH_3$ | $-\langle O \rangle$ | B | Oily product | | $C_{13}H_{19}N_3O_2$ | (a) | | |
| 48 | $-(CH_2)_3CH_3$ | $-H$ | $-CH_2-\langle O \rangle$ | A | 95–96.5 | | $C_{13}H_{19}N_3O_2$ | 62.63 (62.66) | 7.68 (7.77) | 16.85 (16.55) |
| 49 | $-CH_2CH(CH_3)_2$ | $-CH_3$ | $-\langle O \rangle$ | B | 56–57 | 243.5 (20800) | $C_{13}H_{19}N_3O_2$ | 62.63 (62.75) | 7.68 (7.96) | 16.85 (16.82) |
| 50 | $-\underset{\underset{CH_3}{\|}}{CH}-C_2H_5$ | $-CH_3$ | $-\langle O \rangle$ | B | 98–100 | 253 (19900) | $C_{13}H_{19}N_3O_2$ | 62.63 (62.78) | 7.68 (7.96) | 16.85 (16.77) |
| 51 | $-C(CH_3)_3$ | $-CH_3$ | $-\langle O \rangle$ | B | 94–95 | 243 (20100) | $C_{13}H_{19}N_3O_2$ | 62.63 (62.57) | 7.68 (7.84) | 16.85 (16.91) |
| 52 | $-(CH_2)_4CH_3$ | $-CH_3$ | $-\langle O \rangle$ | B | Oily product | | $C_{14}H_{21}N_3O_2$ | (b) | | |
| 53 | $-CH_2CH_2Cl$ | $-CH_3$ | $-\langle O \rangle$ | B | 117–118 | 244 (19200) | $C_{11}H_{14}ClN_3O_2$ | 51.67 (51.66) | 5.52 (5.53) | 16.43 (16.23) |
| 54 | $-CH_2CH_2CN$ | $-CH_3$ | $-\langle O \rangle$ | B | 116–118 | 245 (18800) | $C_{12}N_{14}N_4O_2$ | 58.53 (58.38) | 5.73 (5.59) | 22.75 (22.93) |
| 55 | $-CH_2CH_2N(CH_3)_2$ | $-CH_3$ | $-\langle O \rangle$ | B | 179–181 | 245 (19500) | $C_{13}H_{21}ClN_4O_2$ | 51.91 (51.98) | 7.04 (7.14) | 18.63 (18.46) |
| 56 | $-CH_2CH_2OH$ | $-CH_3$ | $-\langle O \rangle$ | B | 105–106 | 244 (19600) | $C_{11}H_{15}N_3O_3$ | 55.69 (55.68) | 6.37 (6.56) | 17.71 (17.85) |
| 57 | $-\underset{\underset{OH}{\|}}{CH_2C(CH_3)_2}$ | $-CH_3$ | $-\langle O \rangle$ | B | 117.5–119 | 241 (17300) | $C_{13}H_{19}N_3O_3$ | 58.85 (58.94) | 7.22 (7.39) | 15.84 (15.66) |
| 58 | $-\underset{\underset{OH}{\|}}{CH_2}\underset{\underset{OH}{\|}}{CH}CH_2$ | $-CH_3$ | $-\langle O \rangle$ | B | 96–97 | 244 (19700) | $C_{12}H_{17}N_3O_4$ | 53.92 (53.86) | 6.41 (6.66) | 15.72 (15.65) |
| 59 | $-CH_2CH_2OCH_3$ | $-CH_3$ | $-\langle O \rangle$ | B | 52–53 | 243 (16600) | $C_{12}H_{17}N_3O_3$ | 57.36 (57.36) | 6.82 (6.84) | 16.72 (16.71) |
| 60 | $-CH_2COOH$ | $-CH_3$ | $-\langle O \rangle$ | B | 80–82 | 243 (20900) | $C_{11}H_{13}N_3O_4\cdot H_2O$ | 49.07 (48.70) | 5.62 (5.63) | 15.61 (15.48) |
| 61 | $-\underset{\underset{O}{\|}}{C}CH_3$ | $-CH_3$ | $-\langle O \rangle$ | A | 118–120 | 274 (12300) | $C_{11}H_{13}N_3O_3$ | 56.16 (56.19) | 5.57 (5.58) | 17.86 (18.04) |
| 62 | $-OH$ | $-CH_3$ | $-\langle O \rangle$ | B | 128–129 | 245 (18200) | $C_9H_{11}N_3O_3$ | 51.67 (51.53) | 5.49 (5.30) | 20.09 (19.81) |
| 63 | $-OCH_3$ | $-CH_3$ | $-\langle O \rangle$ | B | 115–157 | 243 (17800) | $C_{10}H_{13}N_3O_3$ | 53.81 (53.76) | 5.87 (5.81) | 18.82 (18.57) |

TABLE 1-continued

| Compound No. | $R^1$ | $R^1-NH-\underset{O}{\underset{\|}{C}}-\underset{R^2}{\underset{\|}{N}}-\underset{O}{\underset{\|}{C}}-NH-R^3$ $R^2$ | $R^3$ | Reaction process | Mp. (°C.) | UV$\lambda_{max}^{Cyclohexane}$ m$\mu$ ($\epsilon$) | Molecular formula | Elemental analysis (%) Calculated (Found) C | H | N |
|---|---|---|---|---|---|---|---|---|---|---|
| 64* | –⟨O⟩ | –CH$_3$ | –⟨O⟩ | B | 106–106.5 | | $C_{15}H_{15}N_3O_2$ | 66.90 (67.06) | 5.61 (5.58) | 15.60 (15.67) |

In Table 1, the compounds with * marks are known compounds and thus the remaining compounds are novel ones. Further (a) in the Compound No. 47 and (b) in Compound 52 indicate the following data obtained by NMR and mass-spectrography methods in place of data obtained by elemental analysis.

(a)NMR(CDCl$_3$)$\delta$: 0.88 (3H, m, N$_1$—CH$_2$CH$_2$C-H$_2$—C$\underline{H}_3$), 1.00–1.68 (4H, m, N$_1$—CH$_2$—C$\underline{H}_2$C-H$_2$—C$\underline{H}_3$), 3.18 (2H, m, N$_1$—CH$_2$—CH$_2$CH$_2$CH$_3$), 3.18 (3H, s, N$_3$—CH$_3$), 6.00 (1H, broad, N$_1$—H), 6.88–7.49 (5H, m, Ar—H), 10.62 (1H, broad s, N$_5$—N), MS m/e: 249 (M$^+$).

(b)NMR(CDCl$_3$)$\delta$: 0.88 (3H, broad t, J=6 Hz, N$_1$—CH$_2$—CH$_2$CH$_2$CH$_2$—C$\underline{H}_3$), 1.07–1.92 (6H, m, N$_1$—CH$_2$—C$\underline{H}_2$C$\underline{H}_2$C$\underline{H}_2$—CH$_3$), 2.99–3.27 (2H, m, N$_1$—C$\underline{H}_2$—CH$_2$CH$_2$ CH$_2$CH$_3$), 3.12 (3H, s, N$_3$—CH$_3$), 5.89 (1H, broad t, N$_1$—H), 6.80–7.43 (5H, m, Ar—H), 10.44 (1H, broad s, N$_5$—H). MS m/e: 263 (M$^+$).

Next, several tests for determining the pharmacological properties, in that acute toxicity, anti-pyretic activity, analgesic activity and anti-inflammatory activity of the present 1,3,5-substituted biuret compounds of the formula (1) were conducted and the test results are shown in Table (2). In the tests, each compounds to be tested was used as a suspension in 0.25% carboxymethylcellulose solution. Methods for testing are explained as follows:

1. Acute Toxicity

The ddy strain of male mice (body weight, 20–25 g) were used as test animals. The mice were fasted overnight and the compound to be tested was administered orally. General symptom of the mouse after the administration was observed for 7 days. The lethal dose (mg/kg, body weight) of the test compound was determined in connection with the death number of mice/the number of mice tested. In Table 2, the values indicated with $\Delta$ marks are 50% lethal dose, LD$_{50}$ (mg/kg, body weight).

2. Anti-pyretic Activity

According to the method reported by Tanabe [Folia Pharmacologia Japonica, Vol. 73, pp. 803 (1977)], the Wistar strain of male rats (150–180 g body weight) were used as test animals. The rats were fasted overnight, and 1 ml/100 g (body weight) of 10% dry-yeast suspension were subcutaneously injected on the back of the rats. Five hours afte the injection, the test compound was administered orally, then the body temperature of the rat was measured time sequences. Anti-pyretic activity of the test compound was determined as the FI (febril index) by integrating pyrogenetic curve up to 4 hours after the administration of the test compound with time, and indicated as inhibitory ratio (%) shown by the following formula, $$\text{Inhibitory ratio (\%)} = \left[1 - \frac{\left(\begin{array}{c}\text{FI of the test group}\\\text{of rats administered}\\\text{with test compound}\end{array}\right)}{\left(\begin{array}{c}\text{FI of control group}\\\text{of rats}\end{array}\right)}\right] \times 100$$

3. Analgesic Activity (1) Acetic acid-induced stretching method

According to the method reported by Koster et.al., [Fed. Proc., Vol. 18, pp. 412 (1959)], the ddy strain of male mice (body weight, 20–25 g) were used as test animals. The mice were fasted overnight, 100 mg/kg body weight of the test compound was administered orally, then 1 hour after the administration, 0.2 ml of 0.7% acetic acid solution was injected intraperitoneally. The acetic acid-induced stretching symptom of mouse was observed. Analgesic activity of the test compound was calculated as the inhibitory ratio (%). In Table 2, the values in parentheses show the data obtained from the test by using the dosage other than 100 mg/kg body weight. Further, the values indicated with $\Delta$ marks show 50% effective dose, ED$_{50}$ (mg/kg body weight).

(2) Haffner method

According to the modified method reported by Fujimura et al., [Bulletin of the Institute for Chemical Research, Kyoto University, No. 25, pp. 36 (1951)], the ddy strain of male mice (body weight, 20–25 g) were used as test animals. The mice were fasted overnight, 100 mg/kg body weight of the test compound was administered orally, then 45 minutes after the administration, the threshhold amount (1.5–2.5 mg/kg body weight) of morphine hydrochloride was injected subcutaneously. Then 1-hour pain reaction of the mouse caused by a clamp was observed. Analgesic activity of the test compound was calculated as the inhibitory ratio (%). In Table 2, the values in parentheses show the data obtained from the test by using the dosage other than 100 mg/kg body weight. Further, the values indicated with $\Delta$ marks show 50% effective dose, ED$_{50}$ (mg/kg body weight).

4. Anti-inflammatory Activity

According to the method of acute carrageenin-induced inflammatory test [Folia Pharmacologia Japonica, Vol. 56, pp. 575 (1960)], the Wistar strain of male rats (body weight, 150–180 g) were used as test animals. The rats were fasted overnight, 100 mg/kg body weight of the test compound was administered orally, then 1 hour after the administration, 0.1 ml of 1% carrageenin solution, as the inflammation inducing agent, was injected subcutaneously to the hindpaw of the rat and the volume of the hindpaw was measured at time sequences. Anti-inflammatory activity of the test compound was calculated as inflammation inhibitory ratio (%) at 3 hours after the injection of inflammation inducing agent.

TABLE 2

| Compound No. | Acute toxicity (mg/kg) | Analgesic activity (%) Acetic acid-induced stretching method | Analgesic activity (%) Haffner method | Anti-pyretic activity (%) | Anti-inflammatory activity (%) |
|---|---|---|---|---|---|
| 1* | 2000-2/4 | 37.5 | | | |
| 2* | 500-0/4<br>1000-4/4 | 75 | 50 | | 28 |
| 3* | $\Delta$1448 | $\Delta$35(16–77) | $\Delta$111(66–188) | 145 | 88 |
| 4* | 2000-0/4 | 37.5 | 25 | 79 | 41 |
| 5 | 2000-0/4 | 37.5<br>(200 mg/kg) | 37.5<br>(200 mg/kg) | 28 | 53<br>(200 mg/kg) |
| 6* | $\Delta$1239 | $\Delta$40(21–76) | 50 | 72 | 43 |
| 7 | 1000-0/4<br>2000-3/4 | 62.5 | 12.5 | 121 | 60<br>(200 hours value) |
| 8* | $\Delta$1445 | 87.5 | 50 | 110 | 40 |
| 9 | $\Delta$1084 | 87.5 | 25 | 38 | 46 |
| 10 | 1000-1/4<br>2000-4/4 | 12.5 | | | |
| 11 | 2000-0/4 | 25 | 37.5 | 7 | |
| 12* | 500-0/4<br>1000-4/4 | 100 | 50 | | 47 |
| 13 | 1000-0/4<br>2000-2/4 | 25 | 37.5 | | |
| 14* | $\Delta$656 | 62.5 | $\Delta$145(76–276) | | 54 |
| 15* | $\Delta$1100 | $\Delta$44(21–94) | 62.5 | 94 | 37 |
| 16* | $\Delta$1100 | 62.5 | 25 | | 34 |
| 17* | 1000-0/4<br>2000-3/4 | 25 | 25 | 55 | 33 |
| 18 | $\Delta$1500 | 75 | 25 | 60 | 20 |
| 19 | $\Delta$1400 | 50 | 37.5 | 6 | |
| 20* | 1000-3/4 | 25 | 25 | 112 | 46 |
| 21 | 1000-1/4<br>2000-3/4 | 50 | 37.5 | | 56 |
| 22* | 2000-0/4 | 37.5 | 50 | | 35 |
| 23 | 2000-0/4 | 62.5 | 60<br>(200 mg/kg) | | 49 |
| 24 | 2000-0/4 | 25<br>(200 mg/kg) | 37.5<br>(200 mg/kg) | | 77<br>(200 mg/kg) |
| 25 | 2000-0/4 | 25<br>(200 mg/kg) | 37.5<br>(200 mg/kg) | | 86 |
| 26* | 2000-0/4 | 12.5<br>(200 mg/kg) | 25<br>(200 mg/kg) | | 76<br>(200 mg/kg) |
| 27 | 1000-0/4<br>2000-1/4 | 12.5<br>(200 mg/kg) | 12.5<br>(200 mg/kg) | | 44<br>(200 mg/kg) |
| 28 | $\Delta$1600 | 37.5<br>(200 mg/kg) | 37.5<br>(200 mg/kg) | | 75<br>(200 mg/kg) |
| 29 | 1000-0/4<br>2000-1/4 | 12.5 | 25 | | 31 |
| 30 | 1000-0/4<br>2000-3/4 | | 37.5 | | 30 |
| 31 | $\Delta$1594 | $\Delta$70(44–112) | $\Delta$105(69–159) | 149 | 63 |
| 32 | 1000-2/4<br>2000-4/4 | 100 | 37.5 | 63 | |
| 33 | 1000-0/4<br>2000-4/4 | 62.5 | 25 | 87 | 30 |
| 34 | 2000-0/4 | 25 | 12.5 | | 19 |
| 35 | 1000-0/4<br>2000-4/4 | 87.5 | 62.5 | 112 | 19 |
| 36 | $\Delta$833 | 50 | 62.5 | 43 | 23 |
| 37 | $\Delta$749 | 75 | $\Delta$46(31–69) | 97 | |
| 38 | 1000-0/4<br>2000-3/4 | 87.5 | 25 | 80 | |
| 39 | 2000-0/4 | 50 | 37.5 | 8 | |
| 40 | $\Delta$559 | 75 | 37.5 | 42 | 24 |
| 41 | 2000-0/4 | 62.5 | 37.5 | 65 | 67 |
| 42* | 2000-0/4 | 82.5<br>(200 mg/kg) | 50<br>(200 mg/kg) | | 31<br>(200 mg/kg) |
| 43 | 2000-0/4 | 50 | 25 | 38 | 51 |
| 44 | $\Delta$1400 | 62.5 | 50 | | 33 |
| 45 | 1000-2/4<br>2000-4/4 | 50 | 12.5 | 125 | 59 |
| 46 | 2000-0/4 | | 25<br>(200 mg/kg) | | 84<br>(200 mg/kg) |
| 47 | 2000-0/4 | 75 | 62.5 | 19 | 27 |
| 48 | 2000-0/4 | $\Delta$111(87–141) | $\Delta$110(75–162) | | 46<br>(200 mg/kg) |

TABLE 2-continued

| Compound No. | Acute toxicity (mg/kg) | Analgesic activity (%) Acetic acid-induced stretching method | Haffner method | Anti-pyretic activity (%) | Anti-inflammatory activity (%) |
|---|---|---|---|---|---|
| 49 | 2000-0/4 | 50 (40 mg/kg) | $^\Delta$50(29–83) | 55 | 57 |
| 50 | 2000-0/4 | 62.5 | 25 | 27 | 47 |
| 51 | 2000-0/4 | 50 | 37.5 | 83 | 34 |
| 52 | 2000-0/4 | 62.5 | 37.5 | 38 | |
| 53 | 2000-0/4 | 12.5 | 25 | | 40 |
| 54 | 1000-0/4 2000-3/4 | 50 | 12.5 | | 39 |
| 55 | 500-2/4 1000-3/4 | 12.5 | 12.5 | | 22 |
| 56 | 2000-0/4 | 62.5 | 37.5 | | 42 |
| 57 | 1000-0/4 2000-2/4 | 100 | 50 | | |
| 58 | 2000-0/4 | 37.5 | 37.5 | | |
| 59 | 1000-1/4 2000-4/4 | 25 | 25 | | |
| 60 | 2000-0/4 | 25 | 25 | | |
| 61 | 2000-0/4 | 50 | 12.5 | | |
| 62 | 1000-0/4 2000-1/4 | | 25 | | |
| 63 | 1000-0/4 2000-4/4 | 50 | 25 | | 50 |
| 64* | 2000-0/4 | 37.5 | 12.5 (200 mg/kg) | | |

The followings are examples of preparation for analgesic, anti-pyretic or anti-inflammatory composition containing 1,3,5-substituted biuret compound of the formula (1) as the active ingredient.

| Preparation 1 | |
|---|---|
| Ingredients | Amount (mg) |
| 1,3-Dimethyl-5-phenylbiuret (Compound No. 3) | 200 |
| Lactose | 500 |
| Corn starch | 280 |
| Hydroxypropylcellulose | 20 |
| To make one package contains | 1,000 |

By using the ingredients in the above-mentioned formulation, granular preparation is prepared by conventional methods.

| Preparation 2 | |
|---|---|
| Ingredients | Amount (mg) |
| 1,3-Dimethyl-5-(4-methoxyphenyl)-biuret (Compound No. 8) | 100 |
| Lactose | 85 |
| Crystalline cellulose | 50 |
| Hydroxypropylstarch | 30 |
| Talc | 4 |
| Magnesium stearate | 1 |
| To make one tablet contains | 270 |

By using the ingredients in the above-mentioned formulation, tablet preparation is prepared by conventional methods.

| Preparation 3 | |
|---|---|
| Ingredients | Amount (mg) |
| 1,3-Dimethyl-5-(3-pyridyl)-biuret (Compound No. 15) | 100 |
| Lactose | 50 |
| Potate starch | 50 |
| Crystalline cellulose | 109 |
| Magnesium stearate | 1 |

| Preparation 3 -continued | |
|---|---|
| Ingredients | Amount (mg) |
| To make one capsule contains | 310 |

By using the ingredients in the above-mentioned formulation, a capsule preparation is prepared by conventional methods.

| Preparation 4 | |
|---|---|
| Ingredients | Amounts (mg) |
| 1-Ethyl-3-methyl-5-phenylbiuret (Compound No. 31) | 200 |
| Lactose | 100 |
| Crystalline cellulose | 98 |
| Magnesium stearate | 2 |
| To make one capsule contains | 400 |

By using the ingredients in the above-mentioned formulation, a capsule preparation is prepared by conventional methods.

| Preparation 5 | |
|---|---|
| Ingredients | Amounts (mg) |
| 1-Ethyl-3-methyl-5-(3,4,5-trimethoxyphenyl)biuret (Compound No. 37) | 250 |
| Witepzol W-35 (A trade name for a suppository base material manufactured by and sold from Dynamite Nobel Company.) | 750 |
| To make one suppository contains | 1,000 |

By using the ingredients in the above-mentioned formulation, a suppository preparation is prepared by conventional methods.

Preparation 6

| Ingredients | Amounts (mg) |
| --- | --- |
| 1-(2-Methyl-2-hydroxypropyl)-3-methyl-5-phenylbiuret (Compound No. 57) | 100 |
| Sodium chloride | 16 |
| Distilled water for injection | q.s. |
| To make one ampule contains | 2 ml |

By using the ingredients in the above-mentioned formulation, an injection preparation (ampule) is prepared by conventional methods.

Preparation 7

| Ingredients | Amount (g) |
| --- | --- |
| 1-Ethyl-3-methyl-5-phenylbiuret (Compound No. 31) | 2.0 |
| White vaserine | 23.0 |
| Stearyl alcohol | 22.0 |
| Propylene glycol | 12.0 |
| Sodium laurylsulfate | 1.5 |
| Ethyl p-oxybenzoate | 0.025 |
| Propyl p-oxybenzoate | 0.015 |
| Purified water | q.s. |
| To make the whole | 100 |

By using the ingredients in the above-mentioned formulation, an ointment preparation is prepared by conventional methods.

Preparation 8

| Ingredients | Amount (mg) |
| --- | --- |
| 1-Methyl-3-ethyl-5-phenylbiuret (Compound No. 21) | 100 |
| Lactose | 85 |
| Crystalline cellulose | 50 |
| Hydroxypropylstarch | 30 |
| Talc | 4 |
| Magnesium stearate | 1 |
| To make one tablet contains | 270 |

By using the ingredients in the above-mentioned formulation, tablet preparation is prepared by conventional methods.

Preparation 9

| Ingredients | Amount (mg) |
| --- | --- |
| 1-Ethyl-3-methyl-5-phenylbiuret (Compound No. 31) | 100 |
| Lactose | 50 |
| Potate starch | 50 |
| Crystalline cellulose | 109 |
| Magnesium stearate | 1 |
| To make one capsule contains | 310 |

By using the ingredients in the above-mentioned formulation, a capsule preparation is prepared by conventional methods.

Preparation 10

| Ingredients | Amounts (mg) |
| --- | --- |
| 1-n-Propyl-3-methyl-5-phenylbiuret (Compound No. 41) | 200 |
| Lactose | 100 |
| Crystalline cellulose | 98 |
| Magnesium stearate | 2 |
| To make one capsule contains | 400 |

By using the ingredients in the above-mentioned formulation, a capsule preparation is prepared by conventional method.

Preparation 11

| Ingredients | Amounts (mg) |
| --- | --- |
| 1-Isopropyl-3-methyl-5-phenylbiuret (Compound No. 43) | 250 |
| Witepzol W-35 (A trade name for suppository base material manufactured by and sold from Dynamite Nobel Company) | 750 |
| To make one suppository contains | 1,000 |

By using the ingredients in the above-mentioned formulation, a suppository preparation is prepared by conventional methods.

Preparation 12

| Ingredients | Amounts (mg) |
| --- | --- |
| 1-Propenyl-3-methyl-5-phenylbiuret (Compound No. 45) | 100 |
| Sodium chloride | 16 |
| Distilled water for injection | q.s. |
| To make one ampule contains | 2 ml |

By using the ingredients in the above-mentioned formulation, an injection preparation (ampule) is prepared by conventional methods.

Preparation 13

| Ingredient | Amount (g) |
| --- | --- |
| 1-Isobutyl-3-methyl-5-phenylbiuret (Compound No. 49) | 2.0 |
| White vaserine | 23.0 |
| Stearyl alcohol | 22.0 |
| Propylene glycol | 12.0 |
| Sodium laurylsulfate | 1.5 |
| Ethyl p-oxybenzoete | 0.025 |
| Propyl p-oxybenzoete | 0.015 |
| Purified water | q.s. |
| To make the whole | 100 |

By using the ingredients in the above-mentioned formulation, an ointment preparation is prepared by conventional methods.

What is claimed is:

1. A method of treating a patient requiring analgesia, said method comprising administering to said patient an analgesic amount of a compound of the formula (1):

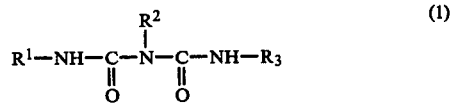

wherein $R^1$ is a hydrogen atom, a lower alkyl group, a substituted lower alkyl group having chlorine atom(s), cyano group(s), dimethylamino group(s), hydroxy group(s), methoxy group(s) or carboxy group(s) as the substituents, a lower alkenyl group, a hydroxy group, a methoxy group, an acetyl group or a phenyl group; $R^2$ is a hydrogen atom, a lower alkyl group or a phenyl group; $R^3$ is a pyridyl group, a substituted pyridyl group having methyl group(s) as the substituent(s) or a pyridyl methyl group.

2. A method of treating a patient having a pyretic or inflammatory condition, said method comprising administering to said patient a therapeutically effective amount of a compound of the formula:

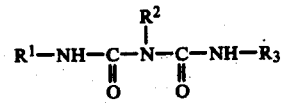

wherein $R^1$ is a hydrogen atom, a lower alkyl group, a substituted lower alkyl group having chlorine atom(s), cyano group(s), dimethylamino group(s), hydroxy group(s), methoxy group(s) or carboxy group(s) as the substituents, a lower alkenyl group, a hydroxy group, a methoxy group, an acetyl group or a phenyl group; $R^2$ is a hydrogen atom, a lower alkyl group or a phenyl group; $R^3$ is a pyridyl group, a substituted pyridyl group having methyl group(s) as the substituent(s) or a pyridyl methyl group.

3. Method of claim 1 or claim 2, wherein said amount is from about 10 to about 2000 mg per day for an adult.

4. Method of claim 1 or claim 2, wherein said daily dosage amount is divided into 2 or 3 portions which are separately administered.

5. Method of claim 1 or claim 2, wherein said compound of the formula (1) is administered orally or topically or by injection or suppository.

6. An analgesic, anti-inflammatory or anti-pyretic composition containing as the active ingredient a 1,3,5-substituted biuret compound of the formula (1)

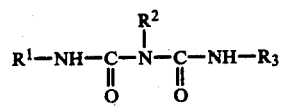

wherein $R^1$ is a hydrogen atom, a lower alkyl group, a substituted lower alkyl group having chlorine atom(s), cyano group(s), dimethylamino group(s), hydroxy group(s), methoxy group(s) or carboxy group(s), as the substituent(s), a lower alkenyl group, a hydroxy group, a methoxy group, an acetyl group or a phenyl group; $R^2$ is a hydrogen atom, a lower alkyl group or a phenyl group; $R^3$ is a pyridyl group, a substituted pyridyl group having methyl group(s) as the substituent(s) or a pyridyl methyl group.

7. Composition of claim 6, wherein said composition is in the form of a tablet, capsule, granules, powder, injection preparation, suppository preparation, topical ointment or cream or peroral syrup, elixir or oily suspension.

* * * * *